United States Patent [19]

Tofield et al.

[11] Patent Number: 4,676,802
[45] Date of Patent: Jun. 30, 1987

[54] METHOD AND APPARATUS FOR SECURING A PROSTHESIS TO THE HUMAN BODY

[75] Inventors: Joshua J. Tofield, 3748 N. Camino Sinuoso, Tucson, Ariz. 85718; Boyd R. Burkhardt, Tucson, Ariz.; Timothy S. Martin, Los Angeles, Calif.; Byron G. Economidy, Tucson, Ariz.

[73] Assignee: J. Tofield, et al., Tucson, Ariz.

[21] Appl. No.: 820,643

[22] Filed: Jan. 21, 1986

[51] Int. Cl.$^4$ .......... A61F 2/00; A61F 5/44; A61B 19/00; A45D 7/00
[52] U.S. Cl. .......... 623/66; 128/1 R; 132/7; 604/332; 604/334
[58] Field of Search .......... 623/11, 66; 132/7, 53, 132/54; 128/1 R, 334 R, 334 C; 433/201.1; 604/332, 334, 338, 277, 328

[56] References Cited

U.S. PATENT DOCUMENTS

| | | | |
|---|---|---|---|
| 3,447,161 | 6/1969 | Weikel | 623/66 |
| 3,663,965 | 5/1972 | Lee, Jr. et al. | 623/11 |
| 3,694,819 | 10/1972 | Meyer | 3/1 |
| 3,758,073 | 9/1973 | Schulte | 623/66 X |
| 3,783,868 | 1/1974 | Bokros | 623/66 X |
| 3,811,425 | 5/1974 | Widdifield | 128/1 |
| 3,862,453 | 1/1975 | Widdifield | 3/1 |
| 3,950,850 | 4/1976 | Driskell et al. | 433/201.1 |
| 4,025,964 | 5/1977 | Owens | 623/66 |
| 4,168,697 | 9/1979 | Cantekin | 128/1 R |
| 4,180,910 | 1/1980 | Straumann et al. | 433/201.1 X |
| 4,183,357 | 1/1980 | Bentley et al. | 623/66 X |
| 4,217,899 | 8/1980 | Freier | 604/332 X |
| 4,261,740 | 4/1981 | Baumel et al. | 128/1 R |
| 4,265,244 | 5/1981 | Hill | 623/66 X |
| 4,321,914 | 3/1982 | Begovac et al | 623/66 X |
| 4,387,705 | 6/1983 | Finney | 128/1 R |
| 4,534,761 | 8/1985 | Raible | 128/1 R X |
| 4,601,701 | 7/1986 | Mueller, Jr. | 604/280 X |

Primary Examiner—Richard J. Apley
Assistant Examiner—Alan W. Cannon
Attorney, Agent, or Firm—Cahill, Sutton & Thomas

[57] ABSTRACT

The method comprises inserting a securing device with skin graft wrapped therearound through an incision in the skin to a subcutaneous region of the body. The skin graft has its epidermis facing the securing device and is joined to the body surface skin at the incision to form a pouch for containing the securing device. The prosthesis is then attached to the securing device. The device comprises a base member for subcutaneous disposition and a post on the base extending to the surface of the body skin. An opening through the post and the base member facilitates attaching the prosthesis to the securing device and permits the pouch to be irrigated by forcing fluid through the opening. Channels in the surface of the base of the device disburse irrigation fluid throughout the pocket for effective cleansing of the pouch. Ridges formed on the post and the base inhibit contractural growth of the pouch from sealing against the securing device and preventing irrigation. The apparatus for attaching the prosthesis to the securing device includes a fastener on the prosthesis with a protuberance adapted to be press fitted into a cavity in a plug sealingly connected to the post in the opening therein by a bayonet connection. The bayonet connection permits the plug to be removed when it is desired to irrigate the pouch.

14 Claims, 4 Drawing Figures

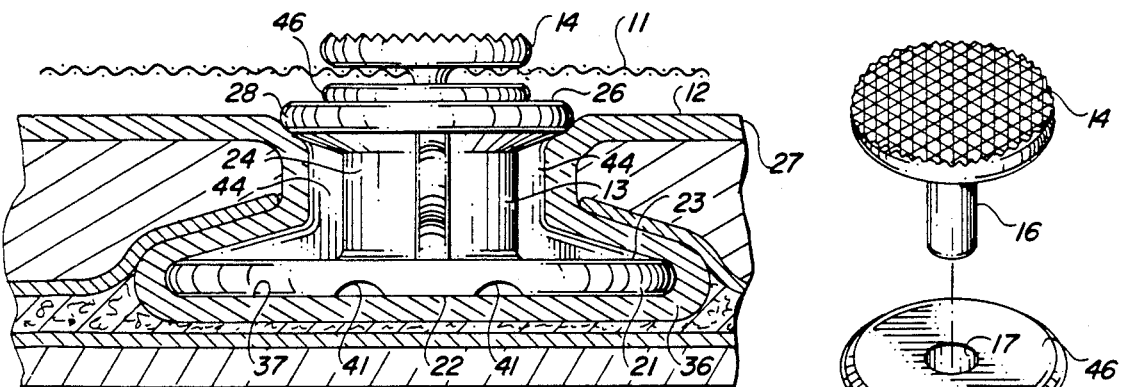
Fig-1
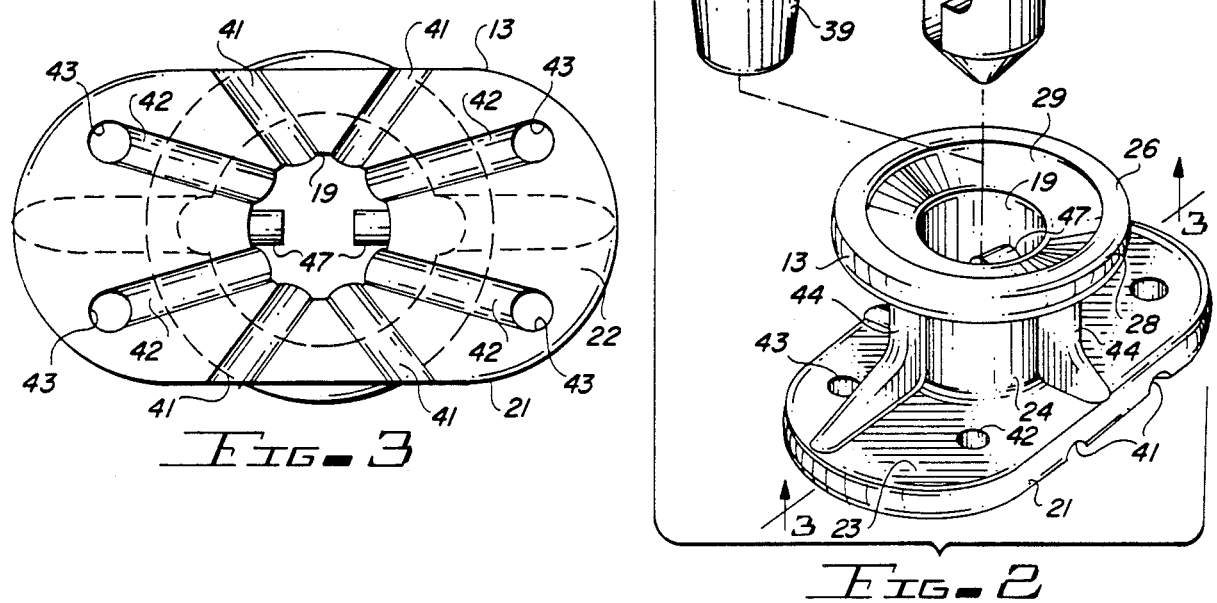
Fig-3
Fig-2
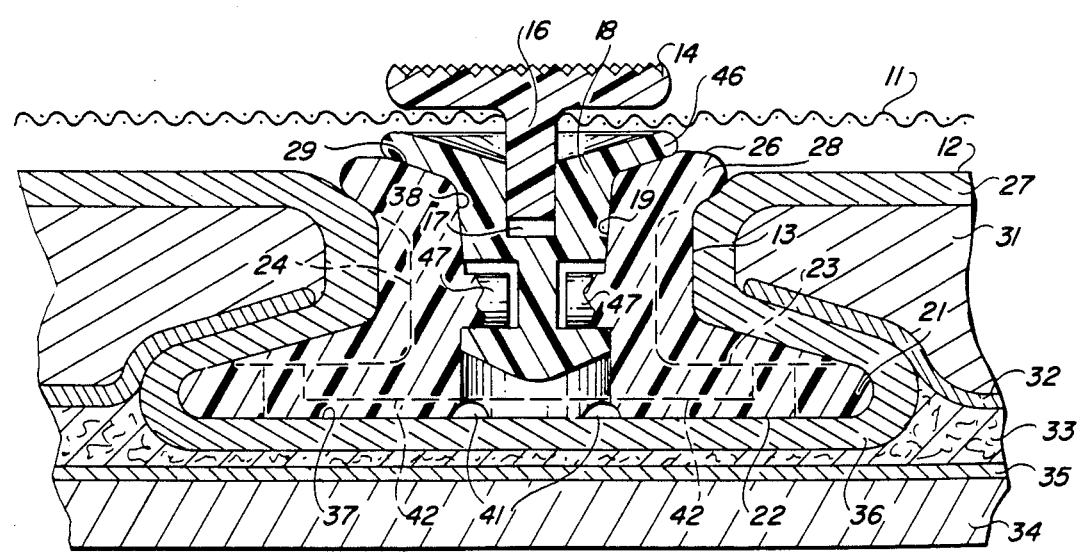
Fig-4

METHOD AND APPARATUS FOR SECURING A PROSTHESIS TO THE HUMAN BODY

TECHNICAL FIELD

This invention is concerned with securement of items to the human body. The invention may be employed for cosmetic purposes to replace missing components or to cover disfigured components of the body. Probably the most common cosmetic prosthesis in use today is the hairpiece, or toupee, employed to cover a partially bald head. The invention is described herein by particular reference to securement of hairpieces, but it is to be understood that the invention can be beneficially employed in the securement of other cosmetic prosthesis, such as, for example, an artificial ear or an artificial breast, and for securing purely functional devices to the body, such as a colostomy appliance.

BACKGROUND ART

There have been numerous proposals for securing prosthesis to the human body by implanting fastener elements beneath the skin in the securement region. U.S. Pat. No. 3,694,819, granted Oct. 3, 1972 to G. P. Meyer for "Hairpiece Securing Device" discloses an attachment system in which an anchor piece is surgically embedded in the scalp. U.S. Pat. No. 3,862,453 granted Jan. 28, 1975 to G. E. Widdifield for "Apparatus for Mounting Hair" discloses a hairpiece attachment system in which an anchor is embedded in the scalp with a flange like base positioned beneath the periosteum cover for the skull. U.S. Pat. No. 3,811,425 granted May 21, 1974 to the same inventor for "Method and Apparatus for Mounting Hair" discloses the surgical technique for implanting this anchor.

Securement systems employing implantable anchors such as those disclosed in the Meyer and Widdifield patents generally have not been successful because of two major problems These are, first, lack of biocompatibility of the implant and second, infection of tissue surrounding the implant. Even the biologically inert materials, such as titanium and pyrolitic graphite, and the supposedly medicinally acceptable materials, such as polyester and silicone, all of which are mentioned in the previously identified patents, usually will be recognized by the body as foreign substances. Even anchors made of biologically compatable materials that are well tolerated by the body when completely buried likely will foster chronic infection and will be extruded when they are partially exposed as they must be to form a component of a securing system for an externally applied prosthesis.

In order to avoid the problems of biocompatibility and infection it has been proposed that the securement system utilize a tunnel formed beneath the surface of the skin and which is lined with a skin graft. Strings or other thin fastener elements are then led through the tunnel and utilized to secure the prosthesis in place. Such attachment elements have proven to be mechanically awkward and virtually impossible to conceal when the prosthesis is not in place. This latter problem is particularly critical for hairpiece wearers who, when electing not to wear the hairpiece prefer not to have unsightly attachment devices protruding from the scalp.

There continues to be a need, therefore, for a method and apparatus for securing the prosthesis to the human body which can be relied upon to provide reliable securement over an extended period of time and which are cosmetically acceptable to the user.

DISCLOSURE OF THE INVENTION

This invention contemplates the use of a securing device having a base which is positioned in a subcutaneous region of the body, but which is not implanted in the body tissue. This is accomplished by a method which involves wrapping the securing device with a reversed skin graft prior to insertion of the device through an incision in the skin. The graft has its epidermis facing the securing device and has its peripheral edge adjacent to the exposed edge of the skin at the incision. This forms a marsupium, or pouch, of skin housing the securing device. A post portion of the securing device extends from the base to the surface of the skin in the securement region and is smaller in cross sectional area than the area of the base of the securing device. The pouch of graft skin thus necks down around the smaller area of the post and firmly holds the base of the securing device in position. The base preferably has a noncircular configuration to resist turning movement in its pouch.

A variety of attaching means can be employed to attach the prosthesis to the post portion of the securing device.

The invention further contemplates that the securing device will have opening means passing from the outer terminus of the post portion thereof to the surface of the base which is opposite the surface to which the post is affixed. This opening means permits fluids to be forced through the securing device and into the pocket to irrigate the pocket for the removal of bacteria and debris therefrom. To insure thorough and uniform cleansing of the interior of the pouch the base of the securing device may have a series of irrigation channels formed in the surface thereof and the post portion and the base of the device may also have ridges formed thereon to reduce the tendency for the skin in the pouch to contract and form a tight, flow restricting seal around the device.

BRIEF DESCRIPTION OF THE DRAWINGS

The invention is described in greater detail hereinafter by reference to the accompanying drawings wherein:

FIG. 1 is a sectional view through a region of a human scalp having the securing system of this invention applied thereto for the purpose of securing a hairpiece prosthesis to the scalp;

FIG. 2 is an exploded perspective view illustrating the various components of the securing system;

FIG. 3 is a view of the underside of the base of the securing device; and

FIG. 4 is an enlarged cross sectional view through the securing system.

BEST MODE FOR CARRYING OUT THE INVENTION

In FIGS. 1 and 4 the numeral 11 designates a scrim forming a part of a hairpiece prosthesis which is to be secured to the scalp 12 of a human. The securing system of this invention comprises generally a securing device, or anchor, 13 and means for attaching the prosthesis to the securing device. The latter means comprises a button 14 positioned over the hairpiece scrim 11 and having a protuberance 16 depending therefrom and extending through the scrim 11 into a cavity 17 in a plug 18 disposed in opening means 19 in the securing device 13.

Securing device 13 comprises a base member 21 having inner and outer surfaces, indicated respectively at 22 and 23, and a post 24 protruding outwardly from the outer surface 23 of base member 21. The base member 21 of the securing device 13 is adapted to be positioned within a subcutaneous region of the body, i.e. beneath the surface of the skin 27 in the region of securement. The post 24 has its outer terminus 26 positioned slightly outwardly of the surface of the skin 27. The outer terminus 26 of post 24 preferably has a flange 28 providing an enlarged conical surface 29 to assist in guiding objects, such as plug 18, into opening means 19 in the post 24.

The method of installing securing device 13 in scalp 12 involves making an incision through the skin 27, through the dense connective fat and fiberous tissue 31 and through the tough membrane of fiberous tissue 32 known as the galea. The incision is such as to permit the base member 21 to be disposed beneath the galea 32 in the loose connective tissue of the scalp. The skull 34 and its periosteum covering 35 are not disturbed.

Prior to insertion of securing device 13 into the incision in the scalp 12 the device 13 is wrapped with a narrow strip of reversed full or split thickness skin graft 36 with the epidermis of the graft facing the securing device 13. Skin graft 36 covers the base member 21 and post 24 of the securing device with the exception of the outer terminus 26 of the post. With the securing device positioned with its base member 21 beneath the galea 32 the edges of the skin graft 36 are sutured to the edges of the scalp skin 27 at the incision. When the skin graft heals there is formed a marsupium, or pouch, 37 containing the securing device 13. The device is positioned such that the outer terminus 26 of post 24 is exposed at the surface of the skin in the opening leading to the pouch. The neck region of the pouch 37 closely surrounds the post 24 of the securing device 13. The base member 21 of the securing device, because it has a larger area than the cross sectional area of the post 24, prevents removal of the securing device from the pouch 37. Moreover, the elongate noncircular configuration of base member 21 (see FIGS. 2 and 3) prevents the securing device from turning in pouch 37.

It can be readily appreciated that with the securing device 13 completely surrounded by the skin graft pouch 37 and isolated from the subcutaneous region of the scalp 12, the securing device, although having a portion disposed beneath the surface of the skin in the region of securement, is not actually implanted in the scalp. In effect, the securing device is externalized with respect to the body tissue beneath the skin and therefore avoids the twofold problem encountered by prior implanted securing devices, namely, bioincompatability and chronic induced infection. Because the securing device 13 is not implanted in body tissue it is not required to be made of exotic materials. It can be molded of inexpensive polycarbonate plastic material.

It is to be expected that the skin graft 36 forming the pouch 37 may harbor bacteria and will shed epithelial cells from its surface. The securing method of this invention and the apparatus utilized therein provide for cleansing the interior of the pouch 37 to periodically remove bacteria and debris which may accumulate therein. Cleansing is performed mechanically by forcing an irrigation fluid into and out of the pouch 37. It will be noted from FIG. 4 that the opening means 19 in post 24 of securing device 13 extends from the outer terminus 26 of the post to the inner surface 22 of base member 21 and provides a passageway to admit irrigation fluid to the pouch 37 at the inner surface 22 of the base member 21. It is preferred that opening means 19 have its outermost region 38 formed with a conventional Luer taper of approximately 2°26' to sealingly receive the nose 39 of a standard medical syringe (see FIG. 2). Irrigant contained in the syringe is forced down through the opening means 19 of the securing device 13, throughout the pouch 37, and exits the pouch through the opening therein surrounding the terminus of post 24 of the securing device. To insure a uniform cleansing action from the flow of irrigant through the pouch, it is desired to provide a number of channels 41 and 42 in the inner surface 22 of base member 21. These channels 41 and 42 communicate at their inner ends with the opening means 19 and radiate outwardly therefrom. Certain of the channels, 41, extend to the transverse side edges of the base member 21 and other channels, 42, may lead to openings 43 extending from the inner surface 22 of base member 21 to the outer surface 23 of that member.

There is a natural tendency for the skin graft 36 forming pouch 37 to grow and contract about the surface of securing device 13. To prevent this contractual growth of the pouch material from forming a sealing relationship with the outer surface 23 of the base member 21 and the exterior of post 24 it is desirable to provide flanges on either one or both of these surfaces. In the preferred mode for carrying out the invention there are provided a plurality of such flanges 44 which extend longitudinally along the outer surface of post 24 and then extend laterally across the outer surface 23 of base member 21 (see FIGS. 1 and 2). The flanges 44 reduce the tendency for the skin graft 36 to seal against the securing device 13 and allow irrigant to flow outwardly along the post 24 and to exit the pouch 37 carrying any bacteria or debris therewith.

Except during periods when the pouch 37 is being irrigated, the opening means 19 through the securing device post 24 is sealed by plug 18, as mentioned previously, to prevent entry of foreign material into the pouch 37. Tight sealing closure of opening means 19 is assured by providing the plug 18 and post 24 with mating fastener components capable of pulling a flange portion 46 on plug 18 into firm engagement with surface 29 at the outer terminus 26 of post 24. Plug 18 and its integral flange 46 are preferably molded of a resilient plastic material, such as a polyester resin, to assure a tight seal. The mating fastener components formed respectively in plug 18 and opening means 19 may simply be mating threads or, in the preferred mode constitute a bayonet type of fastener in which bosses 47 protruding inwardly from the surface of opening means 19 enter cam surface slots 48 in the outer surface of plug 18. With this type of fastener the plug 18 is forced downwardly into opening means 19 and turned a few degrees to lock bosses 47 in the slots 48 to hold plug 18 in the opening means 19.

It is contemplated that several securing devices 13 will be installed in the region of the skin to which the prosthesis is to be affixed. For example, a hairpiece toupee for the average person may require the installation of from 4 to 6 securing devices 13 to assure reliable securement of the hairpiece to the head. These securing devices 13 are usually installed within a region of the scalp having hair remaining thereon so that the devices are not visible even when the hairpiece is not in place.

However, if it is necessary to install securing devices 13 in areas that are likely to be exposed and viewed, their presence can be rendered less obtrusive by having the devices themselves molded of flesh colored materials, or flesh colored plastic covers (not shown) can be provided.

Although the exact size of a securing device 13 is not critical in any sense, it can be formed to a very small size to be less obtrusive. For example, for normal hairpiece securement each device may have an overall height of less than 10 millimeters, a maximum width across the large dimension of the base 21 of less than 18 millimeters and a maximum diameter of the exposed terminus 26 of post 24 of less than 11 millimeters.

After the required number of securing devices 13 have been installed and when the skin grafts are securely healed and the devices have stabilized in their pouches the prosthesis can be fitted. A short projecting marker (not shown) can be inserted in the cavity 17 of each plug 18 and the prosthesis temporarily positioned to mark on the prosthesis the location of the attachment buttons 14. The prosthesis and the markers are removed. The buttons 14 are then installed in the prosthesis in the marked locations, the prosthesis is repositioned and the button protuberences 16 pressed into the cavities 17 in the plugs 18. The prosthesis is thus secured to the body.

At periodic intervals thereafter the prosthesis is removed and the plugs 18 are removed from the devices 13 to permit a syringe containing liquid irrigant to be connected with the opening means 19 in each securing device. A simple press fit between the nose 39 of the syringe and the Luer taper region 38 of the opening means seals the inlet to the opening means and permits the irrigant to be forcefully propelled into and through the pouch 37 containing each securing device to cleanse the pouch.

This cleansing method permits the installed securing devices to remain in place to be utilized over a long period of time without the devices being rejected by the body and with minimal risk of infection in the region of securement.

What is claimed is:

1. A system for securing a prosthesis to the human body, comprising a device positioned within a pouch of human skin disposed beneath the outer surface of the skin in the securement region, said pouch isolating said device from the subcutaneous region of the body, said device comprising a base having inner and outer faces, a post on the outer face of said base adapted to extend to the surface of the skin in the securement region, said post having a cross sectional area less than the area of said base, said post having opening means extending therethrough to the inner face of said base to permit irrigation of the pouch containing said device through said opening means, the arrangement permitting irrigation fluid to flow from said opening means beneath the base of said device throughout the pouch and exit the pouch along said post, the skin of said pouch preventing the irrigation fluid from contacting the subcutaneous region of the body, and means for attaching the prosthesis to said post.

2. The securing device of claim 1 wherein said post has at least one longitudinal ridge on the outer surface thereof to reduce the tendency of the skin in said pouch to seal against the post.

3. The securing device of claim 1 wherein said base has a ridge on the outer face thereof to reduce the tendency of the skin in said pouch to seal against the base.

4. The securing device of claim 1 wherein there is at least one ridge extending longitudinally along the outer surface of said post and across the outer face of said base to reduce the tendency of the skin in the pouch to seal against the device.

5. The securing device of claim 1 wherein said base has a plurality of irrigation channels formed in the inner surface thereof.

6. The securing device of claim 5 wherein said irrigation channels radiate outwardly from said opening means.

7. The securing device of claim 6 wherein at least one of said irrigation channels communicates with an opening in said base extending from the inner surface of the base.

8. The securing device of claim 1 wherein the opening means in said post has a Luer taper to facilitate connection of an irrigating syringe to said securing device.

9. The securing device of claim 1 including removable means for sealing said opening means.

10. The securing device of claim 9 wherein said sealing means comprises a plug adapted to be positioned in said opening means, said plug having a cavity therein, and said attaching means comprises a member carried by the prosthesis and having a protuberance thereon adapted to be press fitted into said cavity.

11. The securing device of claim 10 wherein said post has an inner end attached to said base member and an outer end near the surface of the skin in the securement region and said plug has an outwardly extending flange adapted to sealingly engage the outer end of said post.

12. The securing device of claim 11 wherein said plug is formed of resilient plastic material to facilitate sealing the opening means in said post.

13. The securing device of claim 12 wherein said sealing means and said post have mating fastener components formed therein respectively.

14. The securing device of claim 13 wherein said mating fastener components constitute a bayonet type coupling.

* * * * *